(12) United States Patent  (10) Patent No.:  US 7,047,975 B2
Austin et al.  (45) Date of Patent:  May 23, 2006

(54) FEMALE CONDOM EMPLOYING TENSEGRITY PRINCIPLE

(75) Inventors: Glenn D. Austin, Seattle, WA (US); Lisa Tam, Seattle, WA (US)

(73) Assignee: Path, Seattle, WA (US)

( * ) Notice: Subject to any disclaimer, the term of this patent is extended or adjusted under 35 U.S.C. 154(b) by 470 days.

(21) Appl. No.: 09/921,016

(22) Filed: Aug. 3, 2001

(65) Prior Publication Data

US 2002/0038658 A1  Apr. 4, 2002

Related U.S. Application Data

(60) Provisional application No. 60/223,036, filed on Aug. 4, 2000.

(51) Int. Cl.
*A61F 6/02* (2006.01)

(52) U.S. Cl. .................. 128/844; 602/902; 128/830

(58) Field of Classification Search ............... 128/842, 128/844, 918; 604/347–353
See application file for complete search history.

(56) References Cited

U.S. PATENT DOCUMENTS

| 4,638,790 | A |   | 1/1987  | Conway et al. |
|-----------|---|---|---------|---------------|
| 4,735,621 | A |   | 4/1988  | Hessel |
| 4,805,604 | A | * | 2/1989  | Spery ............... 604/347 |
| 4,834,113 | A |   | 5/1989  | Reddy |
| 4,862,901 | A |   | 9/1989  | Green |
| 4,867,176 | A |   | 9/1989  | Lash |
| 4,895,140 | A | * | 1/1990  | Bellak ............... 600/39 |
| 4,945,923 | A |   | 8/1990  | Evans et al. |
| 4,976,273 | A |   | 12/1990 | Hessel |
| 5,094,250 | A |   | 3/1992  | Hessel |
| 5,228,456 | A |   | 7/1993  | Karg et al. |
| 5,314,447 | A | * | 5/1994  | Papurt ............... 128/842 |
| 5,318,043 | A |   | 6/1994  | Burr et al. |
| 5,325,871 | A | * | 7/1994  | Reddy ............... 128/844 |
| 5,370,633 | A |   | 12/1994 | Villalta |
| 5,433,219 | A | * | 7/1995  | Spery ............... 128/844 |
| 5,490,519 | A |   | 2/1996  | Hessel |
| 5,515,862 | A |   | 5/1996  | Artsi et al. |
| 5,596,997 | A |   | 1/1997  | Abadi |
| 5,622,185 | A |   | 4/1997  | Richardson et al. |
| 5,623,946 | A |   | 4/1997  | Hessel |
| 5,687,741 | A |   | 11/1997 | Torger |
| 5,992,415 | A |   | 11/1999 | Alla et al. |

(Continued)

OTHER PUBLICATIONS

"Who Discovered Tensegrity?", http://tensegrity.com/Who_DiscoveredTensegrity.html 1999, 4 pp., printed from Internet Jun. 28, 2000.

*Primary Examiner*—Michael A. Brown
(74) *Attorney, Agent, or Firm*—Banner & Witcoff, Ltd.

(57) ABSTRACT

Employing the known "tensegrity" principle, a female condom is configured such that when the condom is inserted into a woman's vagina, the woman's introitus acts on a proximal section of an elongated pouch extending between internal and external biasing members (e.g., rings) of the condom. Inward compressive forces exerted by the introitus on the inner ring of the condom cause the inner ring to be pushed distally within the vaginal canal, and the proximal pouch section to become a tension member pulling against the external ring. This causes a "tenting" of the proximal pouch section against the introitus. The resulting interaction of compression and tensile forces (a tensegrity effect) serves to provide the condom with a high degree of internal and external stability, including resistance to twisting and slippage.

37 Claims, 12 Drawing Sheets

U.S. PATENT DOCUMENTS

| | | |
|---|---|---|
| 6,170,484 B1 | 1/2001 | Feng |
| 6,341,607 B1 * | 1/2002 | Couvreur .................... 128/844 |
| 6,520,922 B1 * | 2/2003 | Michelle ..................... 600/562 |
| 6,569,083 B1 * | 5/2003 | Kassman .................... 128/842 |

* cited by examiner

FEMALE CONDOM EMPLOYING TENSEGRITY PRINCIPLE

This application claims the benefit of prior copending U.S. provisional application Ser. No. 60/223,036, filed Aug. 4, 2000.

FEDERALLY SPONSORED RESEARCH AND DEVELOPMENT

This invention was made in part with government support under Cooperative Agreement No. DPE-5968-A-00-0025-00 awarded by the Agency for International Development. The U.S. Government has certain rights in this invention.

BACKGROUND OF THE INVENTION

The present invention relates to barrier methods of human contraception and prevention of sexually transmitted diseases (STDs). More specifically, the invention relates to female condoms, i.e., condoms worn by a woman rather than a man.

Unintended pregnancy and STDs present serious health and social consequences for individuals and society at large. Known prevention and protection measures have reduced these problems to some extent. Male condoms are a well known form of a barrier device that provide varying degrees of protection against unintended pregnancy and STDs. Male condoms, however, generally require the male partner to initiate use after an erection has been attained, thus frequently causing an awkward disruption of intimacy and foreplay. Additionally, many women would prefer not to have to rely on their male partner to provide their protection. Male condoms are disliked for a variety of additional reasons, including reduced sensation for the male partner.

Problems associated with male condoms have led to the development of various forms of female condom that a woman can pre-place in her vagina before intercourse. Unlike a conventional diaphragm or cervical cap, which covers only a region of the vagina near the cervix or the cervix itself, known female condoms generally provide a tubular receptacle extending along the length of the vaginal canal, thereby fully encompassing an inserted penis and affording increased protection. Such devices advantageously empower a woman to protect herself from unintended pregnancy and STDs, without reliance on the male partner.

While known female condoms provide a level of protection and advantage over conventional male condoms, they do not present an ideal solution. Several problems can be identified. Some female condoms are difficult to use and others may be uncomfortable for some women. Both of these problems may reduce the pleasure of intercourse for both the male and the female partner. With many designs, the outside portion of the female condom may shift and twist excessively prior to and during initiation of intercourse. This may require the woman to hold the outside portion with one or both hands during penis insertion, which can be disruptive and awkward. A related problem of known female condoms is a lack of stability of the condom within the vaginal canal. The condoms may move around, and fall partially out, or a portion intended to remain outside of the vagina may be pushed inside. This lack of stability compromises barrier protection, and may make both partners feel nervous and insecure during intercourse.

Hessel U.S. Pat. Nos. 5,490,519 and 5,623,946 disclose tubular devices worn by a female for protection against transfer of infectious matter during sexual intercourse. This general type of condom is available commercially as the REALITY® condom. As shown in FIG. 1 of the present application, these tubular devices have an open end 1 defined by a first ring 3, and a second closed end 5 to be positioned at the distal end of the vagina. The internal tubular portion of the condom is designed to be retained by retaining means positioned at closed end 5, e.g., a second ring 7. Second ring 7 is oriented at an acute angle relative to first ring 3, and is designed to wedge or anchor around the cervix a manner similar to a diaphragm. In use, this ring may slip away from its anchor point and permit a portion of the front part of the condom to hang or dangle outside of the woman user. Also, because the retaining means acts at the distal end of the vagina, security of the first (outer) ring 3 is dependent on the length of the vaginal canal.

Evans et al. U.S. Pat. No. 4,945,923 also discloses a tubular contraceptive device to be worn by a woman. The device includes an outer ring and an inner ring positioned at a closed distal end of the device. The inner ring is, like the Hessel devices, designed to anchor the bottom end of the device around the cervix of a user. It is similarly susceptible to slippage from its cervical anchor point, and twisting or displacement during use.

Another type of female condom, shown in FIG. 2, is commercially available as the REDDY® condom. The REDDY® condom is manufactured in India and has a design generally similar to the REALITY® condom. An outer (proximal) ring 9 of the REDDY® condom is shield-shaped, and retention of an inner pouch 11 is provided by a sponge 13 that is intended to lodge somewhere in the distal region of the vagina near the cervix. The REDDY® condom likewise may lack stability within the vaginal cavity.

Another known type of female contraceptive device is a panty condom 15 as shown in FIG. 3. While providing external stability, these devices do not adequately address the need for stability of the condom pouch within the vagina. A pouch portion 17 that is inserted into the vagina may pull inside out, or twist or turn, which can adversely affect male partner sensation and compromise barrier protection. Additionally, with known panty condoms, air tends to be pumped into the vaginal cavity during intercourse. This can be noisy and uncomfortable for the woman. After intercourse, the devices may turn inside out during withdrawal, thereby making a mess and increasing the potential for disease transmission and unintended pregnancy. Additionally, the panty configuration may be objectionable to users for aesthetic reasons.

Artsi et al. U.S. Pat. No. 5,515,862 discloses a female condom generally similar to the aforementioned panty arrangement. The device has an extensive external shield which is adhesively applied to cover pubic, abdominal, groin, thigh and anal regions, and a flexible tube extending from the shield to a closed end. Multiple rings are positioned along the length of the tube. One ring is used at the closed end to anchor around the cervix, similar to a diaphragm, and additional rings placed along the length of the tube are intended to lodge against the muscular tissue of the vaginal passage, to prevent slippage of the tube along the length of the vagina during use. The disclosed "semi-rigid" intermediate rings may to some extent improve stability of the tube in the vagina canal, yet no guidance is provided with respect to a positioning, sizing or configuration of the intermediate rings to maximize internal/external condom stability. Additionally, multiple rings positioned along the length of the condom may be encountered by a man's penis during intercourse, thus causing discomfort to the male partner.

SUMMARY OF THE INVENTION

In view of the foregoing, it is a principal object of the present invention to provide a female condom having improved external and internal stability, thus increasing the effectiveness of the female condom as a barrier protection device while minimally interfering with, or diminishing the pleasure of, sexual intercourse.

It is a further object of the present invention to provide a female condom as aforesaid, which has a simple, easy to use and unobtrusive structure more likely to gain widespread acceptance.

Still another object of the present invention is to provide a female condom insertion device which facilitates use of female condoms in accordance with the invention.

One or more of these and other objects are achieved by a female condom in accordance with the present invention. A tubular pouch of resilient membranous material has an open end and a closed end. An external biasing member is mounted to the pouch and provides a resilient bias to expand the open end for retaining, in use, the open end external of a vaginal canal. An internal biasing member is mounted to the tubular pouch and provides a resilient bias serving, in use, to expand an intermediate section of said pouch outwardly against a distal portion of a woman's introitus. The tubular pouch includes a distal portion extending between the intermediate section and the closed end, and a proximal portion extending between the open end and the internal biasing member. The internal biasing member is configured and positioned relative to the outer biasing member such that the inner biasing member is, when the condom is installed within a woman's vagina, pushed distally by the introitus to create a force pulling against the outer biasing member, to thereby tent the proximal pouch portion against the introitus.

In a second aspect, the invention is embodied in a method of maintaining within a vaginal canal of a woman, a female condom including a tubular pouch of resilient membranous material having an open end and a closed end, an external biasing member, and an internal biasing member. The method includes inserting a portion of the female condom, including the internal biasing member, into the vaginal canal and permitting the internal biasing member to expand an intermediate section of the condom positioned within the vaginal canal at a distal portion of the woman's introitus. The woman's introitus is permitted to exert inward compressive forces on a proximal portion of the tubular pouch extending between the open end and the intermediate section, such that the proximal portion pulls proximally on the internal biasing member while the introitus presses distally against the internal biasing member. As a result, the proximal portion is tented against the introitus.

In a third aspect, the present invention is embodied in a female condom retained within a vaginal canal of a woman. A tubular pouch of resilient membranous material includes an open end and a closed end. An external biasing member is mounted to the pouch and provides a resilient bias to expand the open end for retaining the open end external of the vaginal canal. An internal biasing member mounted to the tubular pouch provides a resilient bias serving to expand an intermediate section of the pouch outwardly against a distal portion of the woman's introitus. The tubular pouch includes a distal portion extending between the intermediate section and the closed end, and a proximal portion extending between the open end and the intermediate section. The internal biasing member is configured and positioned relative to the outer biasing member, and the introitus, such that the introitus exerts inward compressive forces on the proximal portion causing the proximal portion to pull proximally on the internal biasing member, while the introitus presses distally against the internal biasing member. As a result, the proximal portion is tented against the introitus.

In a fourth aspect, the invention is embodied in an assembly for preplacing a female condom within a vaginal canal of a woman. The assembly includes an inserter device including a tubular housing and a plunger member advanceable within the housing. A female condom is carried within the tubular housing in a collapsed condition such that upon advancement of the plunger member at least a portion of the female condom is pushed out of the tubular housing by the plunger member and permitted to expand from the collapsed condition.

In a fifth aspect, the invention is embodied in a method of adjusting the size of a female condom. The condom includes a tubular pouch of resilient membranous material having an open end and a closed end, an external biasing member connected to the tubular pouch adjacent the open end thereof, and an internal biasing member connected to the tubular pouch distally of the external biasing member. The method comprises adjusting a spacing between the external biasing member and the internal biasing member, by rolling the resilient membranous material upon one of the external biasing member and the internal biasing member.

The above and other objects, features and advantages of the present invention will be readily apparent and fully understood from the following detailed description of preferred embodiments, taken in connection with the appended drawings.

DETAILED DESCRIPTION OF THE PREFERRED EMBODIMENTS

Female condoms in accordance with the present invention are placed in the vagina of a woman to provide a physical barrier to the transfer of fluids between partners during sexual intercourse, to thereby reduce the risks of disease transmission and unwanted pregnancy. The condoms operate uniquely by employing compression and tension forces to provide substantial stability of the female condom, both externally and internally of the vagina. The approach utilized generally joins tension and compression members in a structure that balances the involved forces. The approach utilized is a unique application of the "tensegrity" principle, a general geometric approach developed for buildings and tension framed structures in the 1940's by R. Buckminster Fuller.

Figure 1:
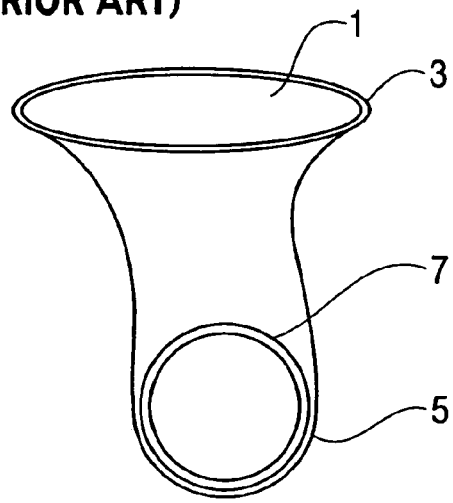
FIG. 1 is perspective view of a prior art female condom device.
Figure 2:
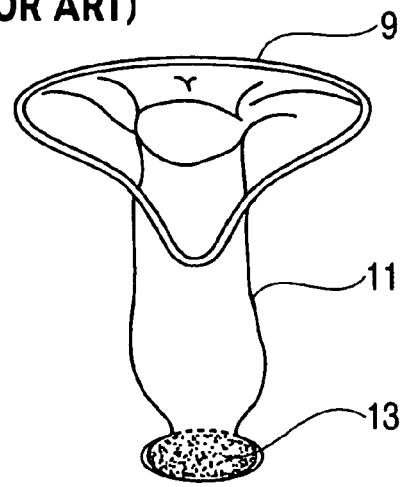
FIG. 2 is a perspective view of a second type of prior art female condom device.
Figure 3:
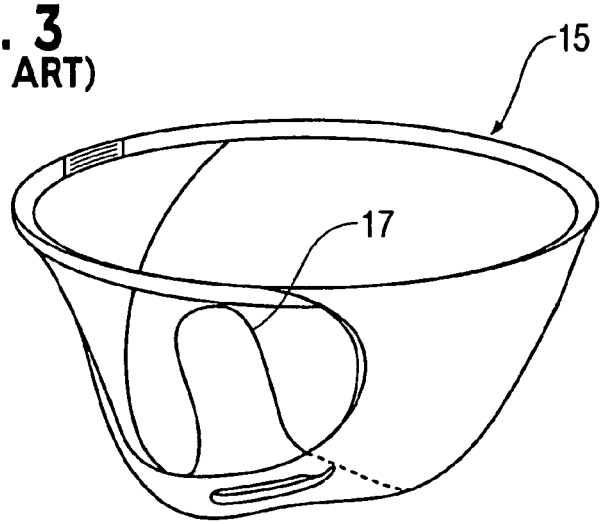
FIG. 3 is a perspective view of a third (panty-style) prior art female condom.
Figure 4:
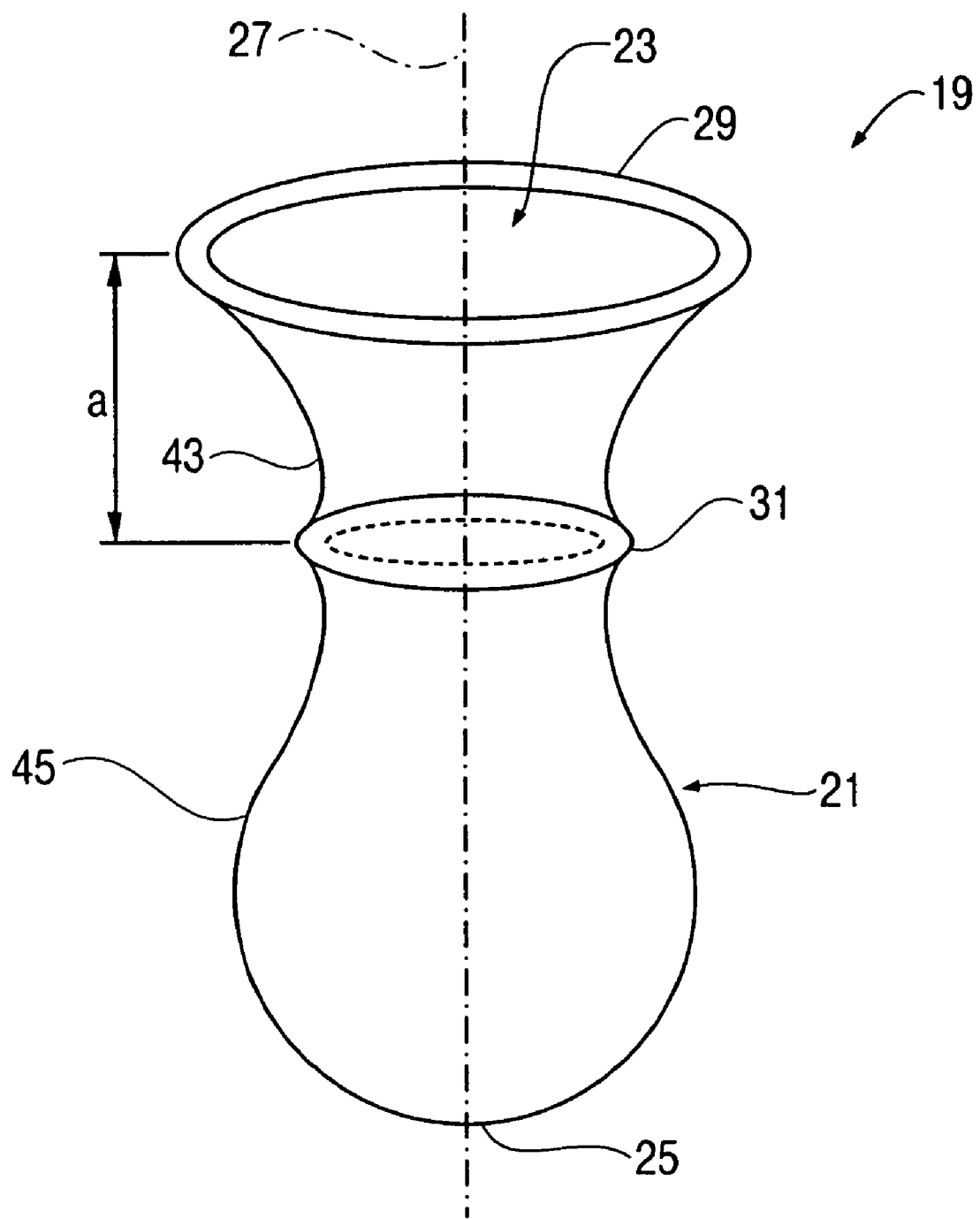
FIG. 4 is a perspective view of a female condom in accordance with the present invention.
Figure 5:
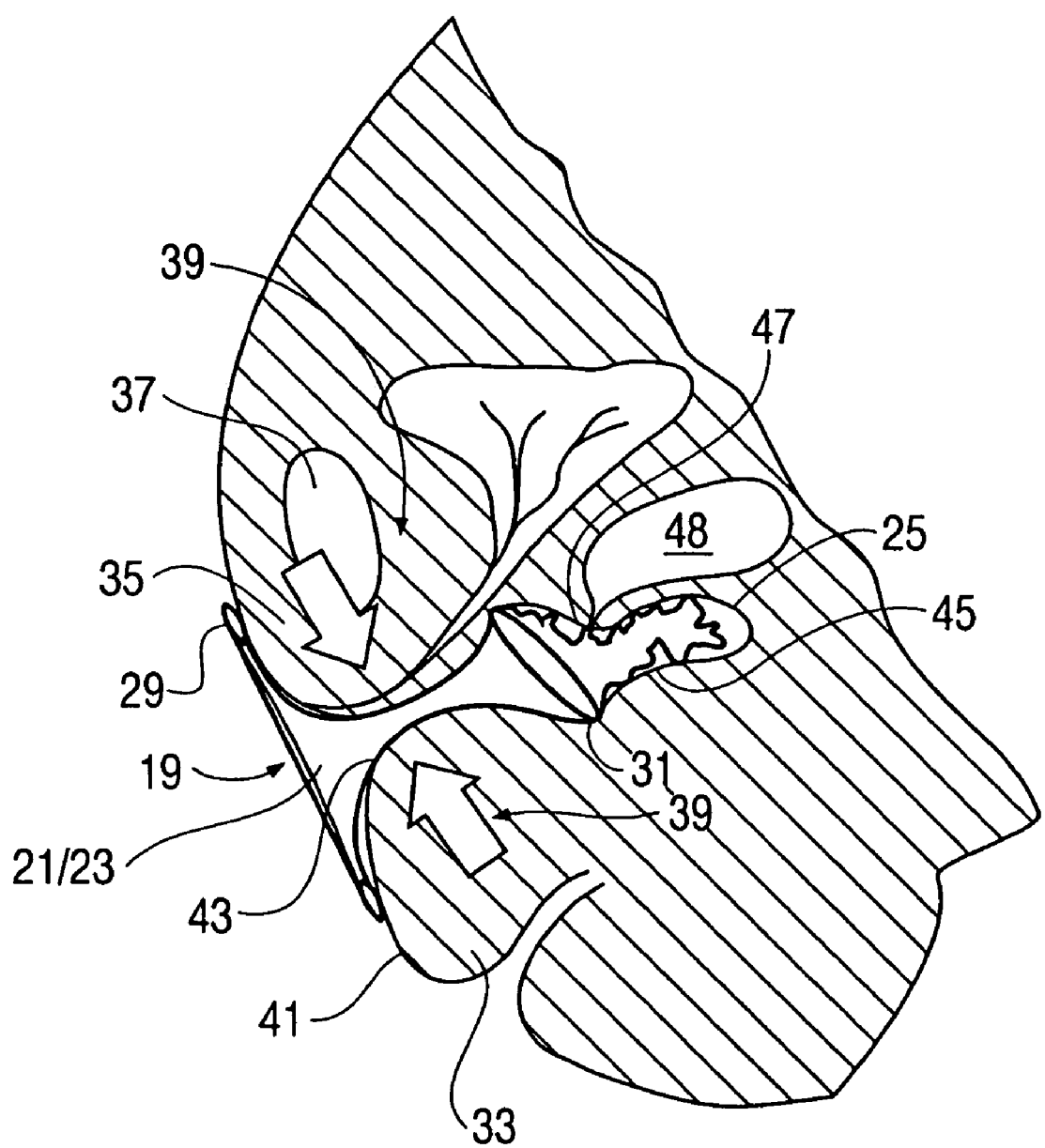
FIG. 5 is a cross-sectional view illustrating portions of the female anatomy and showing the female condom of FIG. 4 positioned for use.

Referring first to FIG. 4, a female condom 19 in accordance with the present invention comprises an elongated tubular pouch 21 of thin membranous material. Pouch 21 has an open end 23, a closed end 25, and a central longitudinal axis 27. Condom 19 further includes an outer resilient ring 29 secured about open end 23, and an inner resilient ring 31, smaller in diameter than ring 29, secured about a circumference of tubular pouch 21. Inner ring 31 is disposed concentric with outer ring 29 with respect to longitudinal axis 27. Inner ring 31 is sized, configured and spaced from outer ring 29 in particular relation to portions of the female anatomy, namely, the proximal portion of vaginal canal in the area of the sphincter muscles 33, vaginal sling muscles 35 and the pubic bone 37, collectively referred to herein as the introitus 39 (see FIG. 5). As shown in FIG. 5, outer ring 29 is sized such that, in use, it remains disposed external, generally contacting the region surrounding the vaginal opening (the vulva), and the perineum 41 of the female user. Inner ring 31 is configured and disposed in relation to outer ring 29 such that when female condom 19 is inserted into the vaginal canal and is fully deployed, ring 31 locates itself and presses against inclined vaginal wall surfaces at a distal side of introitus 39.

The rings should be relatively soft (e.g., Shore A 40–100 durometer), but should exert a minimum amount of spring energy to push against (and open) pouch 21 and the surrounding vaginal tissue. Preferred properties of the ring material are indicated in the following table.

|  | ASTM Standard | Units | Tight Range | Broad Range | Current Polyurethane Candidate(s) (PU Condom) | Current Thermoplastic Elastomer Candidate (PE Condom) |
|---|---|---|---|---|---|---|
| Mechanical |  |  |  |  |  |  |
| Flexural Modulus, 1% Secant | D790 | psi | 5000–15000 | 0–50000 | 5840–14100 | 11000 |

-continued

| | ASTM Standard | Units | Tight Range | Broad Range | Current Polyurethane Candidate(s) (PU Condom) | Current Thermoplastic Elastomer Candidate (PE Condom) |
|---|---|---|---|---|---|---|
| Elastomer | | | | | | |
| Compression Set (@73 Degrees F.) | D395 | % | 0–25 | 0–50 | 20–24 | Not available |
| Tensile Stress @ 100% Hardness | D412 | psi | 500–1500 | 0–5000 | 1000–1500 | Not available |
| Durometer Hardness | D2240 | A Scale | 70–90 | 40–90 | 85–90 | 61 (41 Shore D) |

Outer ring 29 preferably has an inside diameter of about three inches, but that diameter could vary from 1.5–4.5 depending on the material, shape, and softness of the ring. Inner ring 31 preferably has an inner diameter of about 2, but that diameter could vary from 1.4–3. The inventors originally identified a preferred untensioned (at rest/pre-insertion) spacing between the two rings (a) of about 3.25, and a preferred range for the same of 2.5–3.75. It is believed that, on average, adult women will have an introitus 39 with a total depth of tissue of about 2.25. An untensioned spacing (a) of 3.25 will provide, in use, a spacing between the rings approximately equal to the 2.25 total depth of tissue, taking into account the curvilinear distance along the bell or hour-glass shape of pouch 21 created when condom 19 is in place (see FIG. 5). A somewhat larger inter-ring spacing, within the range of 3.75–5.0, and most preferably 4.25, has since been found desirable to avoid adverse influences of the introitus on the ability of the inner ring to open upon insertion. The inventors have come to understand that the influence of the introitus extends more deeply into the vaginal canal than the total depth of tissue of the introitus.

The overall pouch preferably has a minimum diameter of 2 and a length of 7; the minimum diameter may range from 0.8–3, and the length may range from 4–10. An untensioned (pre-insertion) hour-glass or "waisted" shape is desirable to conform more closely to the shape assumed in use, with inner ring 31 positioned at the waist (minimum diameter section). The pouch can be straight-sided. However, a preformed hour-glass shape will reduce radial wrinkling when the device is in place. It is believed that this will contribute to a better fit by providing more contact with the introitus, and more range of fit due to the increase in material length for a given inter-ring spacing.

Referring to FIGS. 4 and 5, tubular pouch 21 includes a proximal section 43 extending between outer ring 29 and inner ring 31, and a distal portion 45 extending from inner ring 20 to closed end 24. Proximal section 43 serves, in use, as a tension member for securely and stably retaining the condom in the vagina during use. Distal section 45 has a bulbous shape which, in the illustrated embodiment, is permitted to collapse loosely in the distal end of the vaginal canal adjacent the cervix 47 (and uterus 48). Both proximal section 43 and distal section 45 will open freely to accommodate, without interference, a penis during intercourse.

So constructed, when female condom 19 is positioned for use in a woman's vagina, introitus 39 creates a zone of influence that is advantageously utilized by female condom 19. Introitus 39 tends to collapse the vaginal walls so as to exert a uniform inward compressive force on proximal pouch section 43, and inner ring 31. When condom 19 is positioned for use, both rings exert gentle expansion forces tending to create and maintain stable ring shapes in generally flat planes, with the topside of the inner ring usually canted slightly proximally relative to (toward) the outer ring. (An angle of up to 45° may be formed between the rings, or the rings may be generally parallel, depending on the anatomy of the user.) The rings are expanded, and proximal pouch section 43 is stretched in tension. More specifically, the inwardly directed compressive forces exerted by introitus 39 on proximal section 43 cause proximal section 43 to pull proximally on inner ring 31. At the same time, introitus 39 presses distally against inner ring 31. For example, the generally inclined orientation of the vaginal wall surfaces in the distal region of introitus 39 may cause a "squeezing" effect serving to push inner ring 31 distally within the vaginal canal. These interactions create a pulling force across proximal pouch section 43, and against outer ring 29 which is retained externally of the vagina. This causes a "tenting" of proximal section 43 against the introitus 39, whereby proximal pouch section 43 takes on the general shape of an hour-glass (even if initially straight-sided). Inner and outer rings 31, 29 pull against one another, and against the outer surface of perineum 41 and inner (distal) surfaces of introitus 39 (sphincter, pubic bone, vaginal sling muscle, etc.). The countervailing forces balance one another holding the condom firmly in place. In accordance with the general tensegrity principle, proximal pouch section 43 serves as a tension member, and outer and inner rings 29 and 31 serve as compression members. The balanced interplay of the resultant tensile and compressive forces, together with the contact of outer ring 29 with perineum 41, and the contact of proximal pouch section 43 and inner ring 31 with the vaginal walls in the region of the introitus 39, serve to provide both internal and external stability of the female condom, including resistance to twisting and slippage prior to and during intercourse.

Advantageously, a high degree of stability may be achieved with a simple unobtrusive structure. External anchoring structure such as a panty configuration or adhesive securement is unnecessary. Moreover, in contrast to multi-ring condoms of the prior art, use of a single internal ring positioned at the distal side of the introitus 39 positions the ring close-enough to the vaginal opening that there is minimal risk of penis-ring interference during intercourse.

The rings and pouch of female condom 19 are preferentially made of the same or a compatible elastomeric material.

This material may be thermoplastic urethane, polyolefin, or any of a number of thermoplastic elastomers. The materials may also be thermosetting elastomers such as urethane, latex, or silicone. Use of elastomers, e.g., latex, with a high degree of stretchiness (i.e., low modulus and high elongation under relatively low loads) may be desirable in order to enhance the fit achieved throughout a larger range of variation in the female anatomy. The pouch material is preferably cast or extrusion-blown film, which should be thin enough to assure reasonable sensation for the partners (0.0005" to 0.004"). It may be textured (e.g., molded with corrugations, ridges or other texture) for added sensation, and to provide an enhanced ability to hold lubricants.

The pouch and rings may be molded together of a unitary pouch/ring material, or with the rings provided as mold inserts, using a blow molding or dipcasting technique. Alternatively, the pouch and rings may be fabricated separately and joined using heat welding or adhesives. The latter approach is presently preferred in order to achieve very thin membranes. If fabricated separately, inner ring 31 preferably is attached to pouch 21 on an outside thereof, to minimize the possibility of interference with an inserted penis. The pouch itself may be seam welded in a flat pattern or formed (drape, pressure, or vacuum formed) from a flat sheet.

Preferably, the rings will be constructed of a homogeneous material, but they could also have stiffener elements or spring inserts made of polymers or stainless steel. The rings are preferably shaped for optimal comfort for both partners. Outer ring 29 is preferably made of a low profile rounded cross-section, while inner ring 31 is preferably more of a rounded band shape to assure maximal stability, ease of handling when folding, and low profile (especially on the inner side) to avoid discomfort to the male partner. Optionally, the cross-section of both rings may be round, flattened, bands, half-round, ovoid, rectangular, irregular, or contoured. FIGS. 6A–6M show some examples of the wide range of possible ring cross-sections. Preferences for use of these shapes in the inner/outer rings is indicated below.

6A—Outer
6B—Inner
6C—Outer
6D—Inner
6E—Inner
6F—Inner
6G—Inner
6H—Either
6I—Either
6J—Inner
6K—Inner
6L—Inner
6M—Inner The preferred maximum cross-sectional dimensions for the outer ring are 0.08 by 0.11, but may range from 0.025 to 0.25. The preferred maximum cross-sectional dimensions for the inner ring are 0.12 by 0.07, but may range from 0.25 to 0.025 depending on the material and desired anatomical fit characteristics.

Figure 6A:
FIGS. 6A–6M are partial cross-sectional views illustrating a variety of possible ring shapes useable in the inventive female condoms.
Figure 6B:
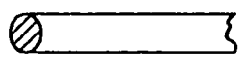
Figure 6C:
Figure 6D:
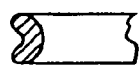
Figure 6E:
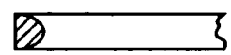
Figure 6F:
Figure 6G:
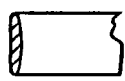
Figure 6H:
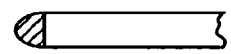
Figure 6I:
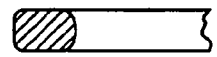
Figure 6J:
Figure 6K:
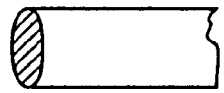
Figure 6L:
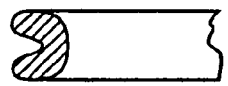
Figure 6M:
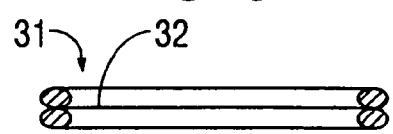

Referring to FIG. 6M, inner ring 31 may comprise a double ring structure. Such a structure may add stability so as to facilitate squeezing by the user prior to insertion, and reduce the height of the cross-sectional profile, thus minimizing the possibility of interference or discomfort as a result of penile contact during intercourse. A groove 32 formed between the pair of joined rings advantageously forms a tactile structure that a user may more easily grip. The double ring structure may be formed by heat welding or adhesively connecting two like rings, or by molding the entire structure as a single piece. A preferred variation on the cross-sectional shape of FIG. 6M is illustrated in FIG. 6L. As shown, a backward "B" shape provides a smooth inner surface and a double-humped outer surface providing a tactile structure similar to the embodiment of FIG. 6M. Similar tactile structures are provided by the outwardly facing concave surfaces of the rings of the FIG. 6D and 6F embodiments.

Figure 7:
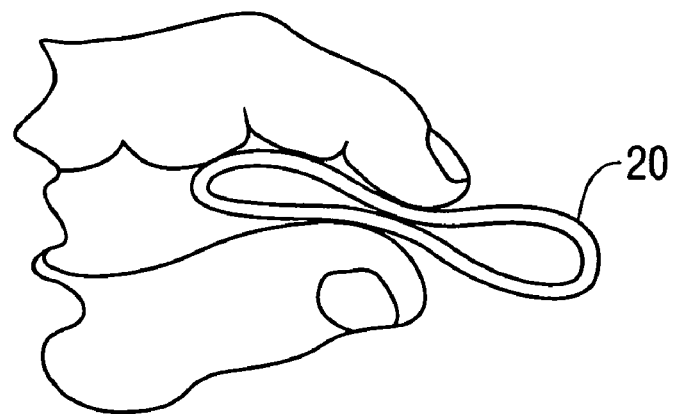
FIG. 7 is a side elevational view demonstrating a technique for folding an inner ring of a female condom in accordance with the present invention, prior to direct insertion of the condom by hand.

Referring to FIG. 7, to use female condom 19, the user may squeeze inner ring 31 between her thumb and index finger to fold the same into a bow-tie configuration, and insert it into her vagina much like a diaphragm or tampon. (As will be described, ring 31 may also be pre-folded and contained within an insertion device or package.) Once inside the vagina, inner ring 31 will expand and find a position where it exerts a balanced pull against outer ring 29. Proximal pouch section 43, formed between the two rings, will take on an hour-glass shape, with its narrowest section at a central part of the introitus. This narrowest section will have a diameter in the range of 0.2 to 1.2, typically about 0.5. In addition to its retaining and stabilizing function, an hour-glass shape of proximal pouch section 43 also advantageously forms a funnel-like entry path for the penis. Advantageously, distal pouch section 45 of pouch 21, which extends beyond inner ring 31, need not be anchored in the manner of prior devices, but rather may be permitted to rest loosely within the distal region of the vagina. Distal pouch section 45 may be deployed along the vaginal canal with a finger, if desired, or by insertion of a partner's penis during intercourse.

For purposes of packaging, distal pouch section 45 may be pleated, rolled, or bunched and contained temporarily within inner ring 31. Retention may be accomplished by a thin break-away band of the pouch material, or by a small sub-pouch molded into the device. Such temporary containment will prevent the distal pouch material from interfering with insertion of the inner ring, and permit distal section 45 to be easily deployed along the vaginal canal by a finger or penis.

Figure 8:
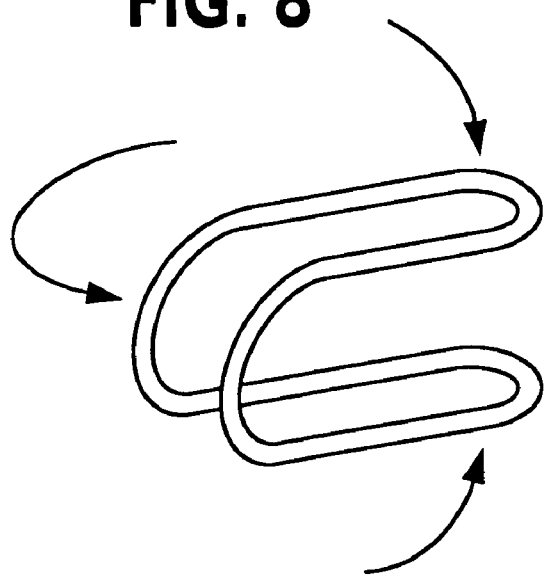
FIG. 8 is a diagrammatic perspective view of a ring of the invention (inner or outer) folded about two axes for insertion into an inserter device.

Female condom 19 may come packaged for distribution/sale with the rings folded into any shape that avoids kinking and which permits resilient restoration of the rings to their original shape, e.g., a single, double, or triple folded condition. A double-folded condition is illustrated in FIG. 8. Prefolding the inner ring may facilitate insertion of the condom by avoiding the need for user-folding of the inner ring. After insertion, the inner ring may expand by being released from an integral pouch, or by the breaking of a break-away band. Lubricant or adhesive coatings may be added to condom 19 to enhance use or add stability to selected portions of the device. Spermicides may be added to any lubricants, adhesives, or inserted sponges, or integrated into the pouch film or the rings themselves.

Figure 9A:
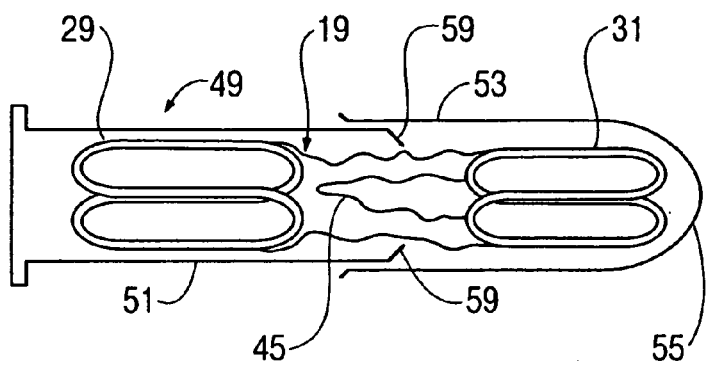
FIGS. 9A–9C are sequential side elevational views showing a female condom of the invention being deployed with an inserter device (shown as transparent for clarity).
Figure 9B:
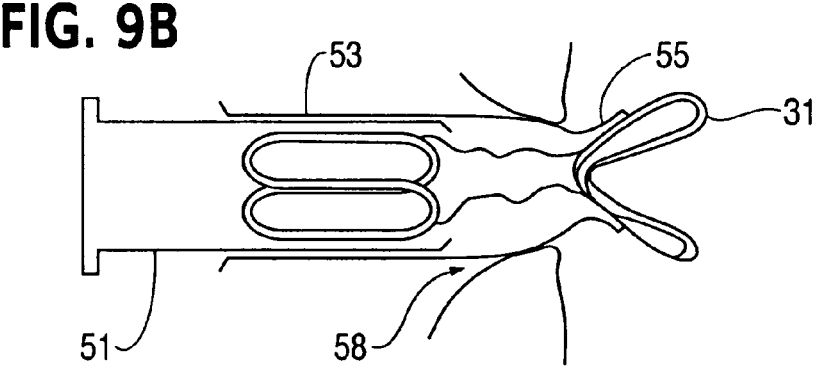
Figure 9C:
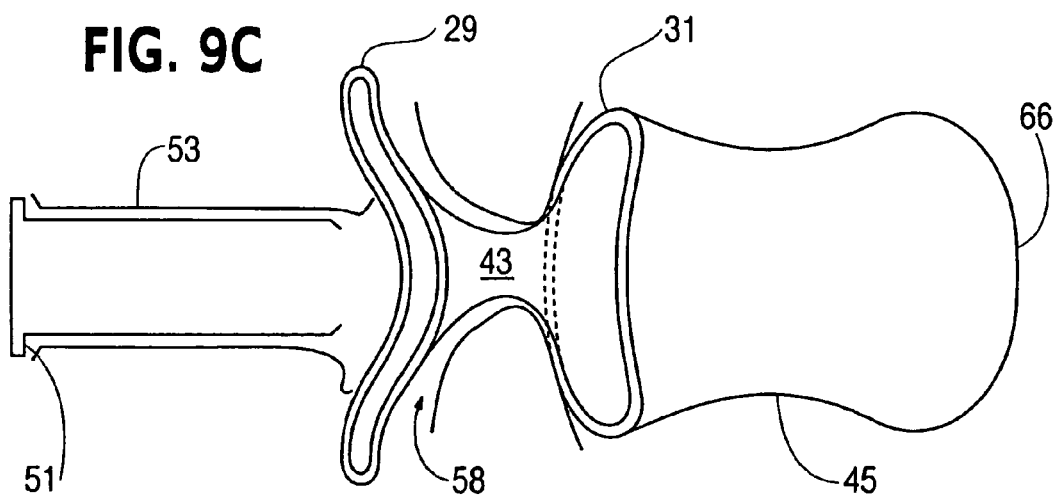

An inserter device 49 may be used to place female condom 19 in the vaginal canal, as shown in FIGS. 9A–9C. Female condom 19 is shown, respectively, in a first position prior to vaginal insertion, in a second position with the distal end of the condom exiting the inserter and entering the vaginal canal, and a third position where the condom has fully exited the inserter and has been placed in position for use.

Figure 10:
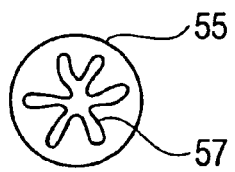
FIG. 10 is a front end elevational view of the inserter shown in FIGS. 9A–9C.

Inserter device 49 is generally tubular and constructed of a biocompatiable material, such as plastic or stainless steel. Female condom 19 is carried inside of device 49 with each of the rings 29 and 31 held in a double-folded condition. Inserter device 49 operates generally similar to a conventional tampon inserter. Inserter device 49 has an inner plunger 51 slidably disposed inside of an outer housing 53. As shown in FIG. 10, a distal end 55 of inserter device 49 (housing 53) has a resilient generally star-shaped exit port 57 through which female condom 19 passes during insertion.

FIG. 9A shows inserter device 49 and female condom 19 in a first prepackaged ready-for-use condition. FIG. 9B shows inserter device 49 in a second position wherein the distal end 55 of inserter device 49 has been inserted into the vagina 58 to a position proximal the distal end of introitus 39 (see FIG. 5). Plunger 51 has been advanced to cause inner ring 31 to exit the inserter through resilient opening 57. As plunger 51 is advanced distally within outer housing 53, a pushing element, e.g., a ledge 59 formed by in-turned leading edges of plunger 51, contacts inner ring 31 and pushes the same through port 57.

FIG. 9C shows female condom 19 just released from inserter device 49 and deployed into the vagina. This condition is achieved by pulling the inserter device proximally away from the vaginal opening, following insertion/expansion of inner ring 31. Inner ring 31 anchors the condom device within vagina 58. Ledge 59 and port 57 are sufficiently resilient to permit passage of the remainder of female condom 19, including outer ring 29, out of inserter 19 as the inserter is pulled proximally away from vagina 58.

Figure 11:
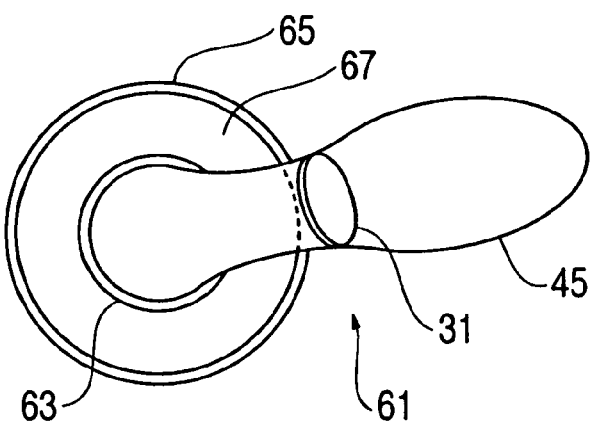
FIG. 11 is a perspective view of an alternative female condom embodiment in accordance with the invention, having an outer shield formed between a pair of concentric outer rings.

With reference to FIG. 11, a modified female condom 61 in accordance with the invention has an outer shield-like structure including a resilient outer ring 63, a larger diameter generally concentric ring 65, and membranous pouch material 67 extending therebetween. Such a shield-like structure may be used, in place of a single outer ring (as in the previous embodiments) to provide additional coverage/protection of the external genitals.

Figure 12:
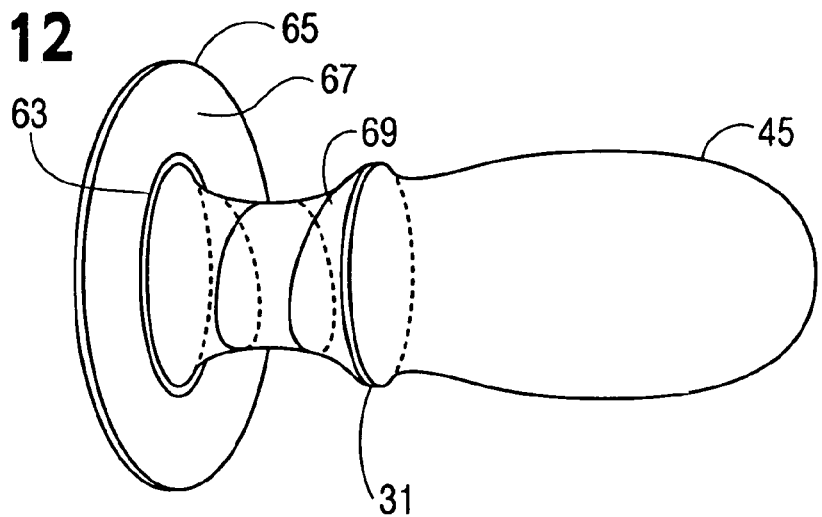
FIG. 12 is a perspective view of a female condom embodiment as shown in FIG. 11, including additional supporting framework in the form of a helical coil extending between inner and outer rings.
Figure 13:
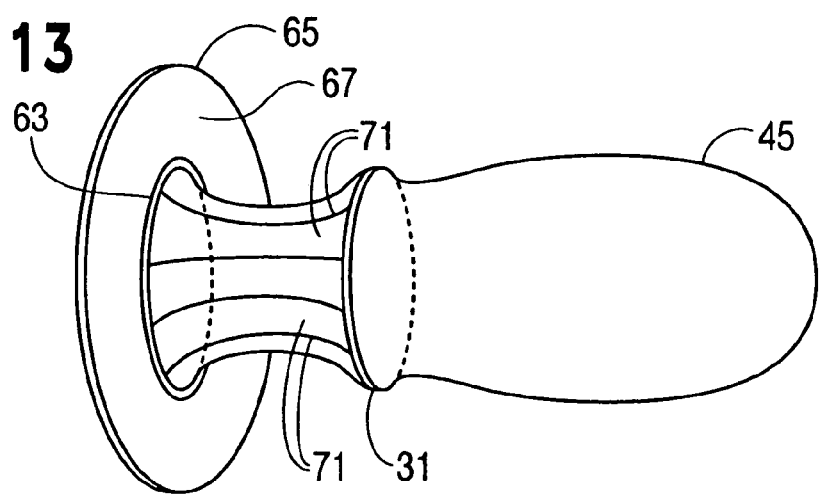
FIG. 13 is a perspective view of a female condom embodiment similar to the FIG. 12 embodiment, having additional supporting framework in the form of a plurality of fibers extending lengthwise between inner and outer rings.

With reference to FIGS. 12 and 13, inner ring 31 and outer ring 63 may be connected by a fine framework in addition to the pouch membrane. Fibers or fine ribs may extend along proximal pouch section 18 and join the rings. A single element 69 may extend about proximal section 43 in a helical manner (see FIG. 12). Alternatively, a plurality of fine framework elements 71 may extend longitudinally between the rings (see FIG. 13). Such elements can serve to provide, with the pouch membrane, an elastomeric composite structure increasing the strength and/or stretchiness of the condom in proximal section 43.

Figure 14:
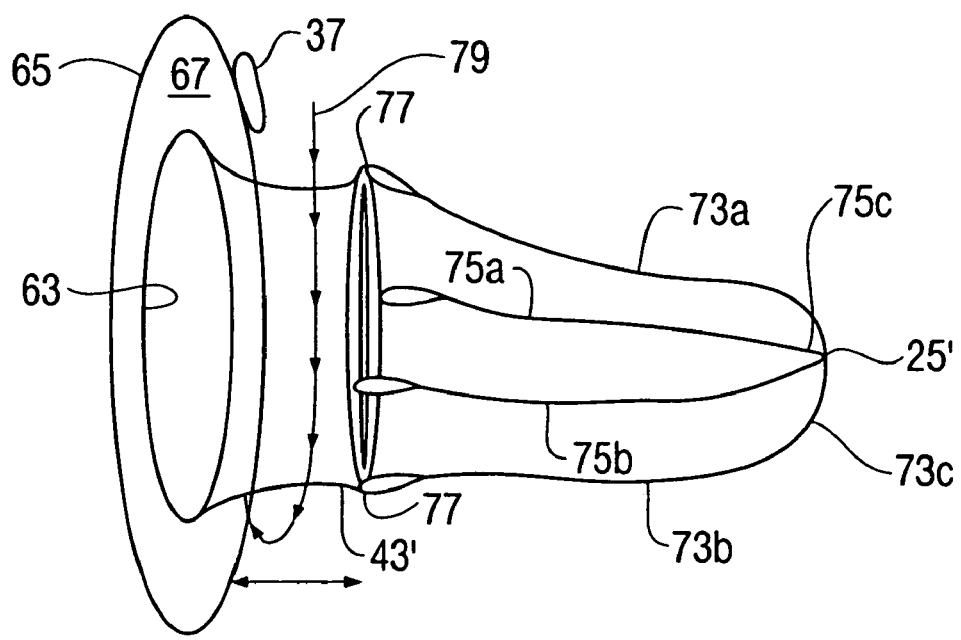
FIG. 14 is a schematic diagram of an alternative female condom embodiment in accordance with the invention including elastic stays substituted for an inner ring, and showing operative tension forces created through use of the condom.

FIG. 14 shows an alternative embodiment of the invention, wherein elastic stays are substituted for the inner ring of the previous embodiments. In the illustrated embodiment, four equi-spaced legs 73a,b, 75a,b of a pair of orthogonally arranged generally U-shaped stays 73, 75 extend longitudinally along the sides of distal pouch portion 45 and terminate at an intermediate pouch section 77 corresponding to the position of inner ring 31 of the previous embodiments. Arcuate connecting portions 73c, 75c extend radially about closed end 25 serve to provide the stay legs with an outward biasing force tending to create a flared (badminton birdie-like) structure having a maximum diameter at intermediate pouch section 77. As with the inner ring of the previous embodiments, the position of pouch section 77 is chosen such that when the condom is positioned for use, section 77 will press against the vaginal walls at a distal side of the introitus, thus pushing section 77 distally and causing a "tenting" of the proximal pouch section 43 against the vaginal walls in the region of the introitus. The resiliently flared structure of this embodiment permits the condom pouch to be compressed radially inwardly for insertion, and causes the pouch to automatically expand radially against the vaginal walls upon insertion. For removal, the user may reach in and pull inward on one or more of the legs to collapse the structure. Alternatively, a graspable drawstring could be arranged around the ends of the legs to permit collapse all of the legs together. In FIG. 14, the zone of influence of the introitus on proximal pouch section 43 is schematically depicted by force line 79. As with the rings and other frameworks previously described, stays 73, 75 may be formed (e.g., molded) integrally with the pouch material, or may be formed separately from the pouch material and subsequently joined thereto.

Figure 15:
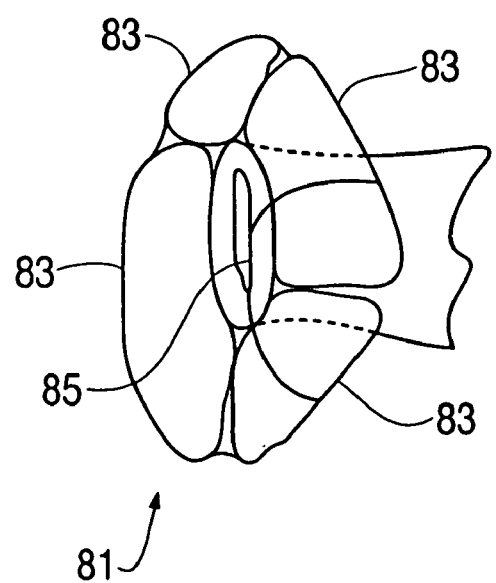
FIG. 15 is a partial perspective view of a further female condom embodiment in accordance with the invention, including multiple soft hoops serving as shield forming external biasing members.
Figure 16:
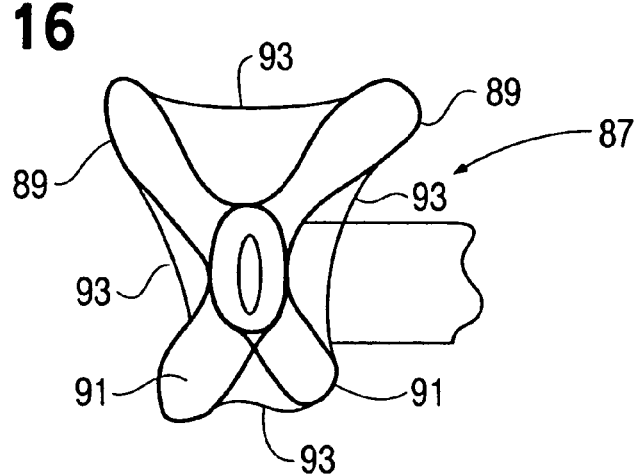
FIG. 16 is a partial perspective view of a further female condom embodiment in accordance with the invention, including multiple finger-type springs serving as shield-forming external biasing members.
Figure 17:
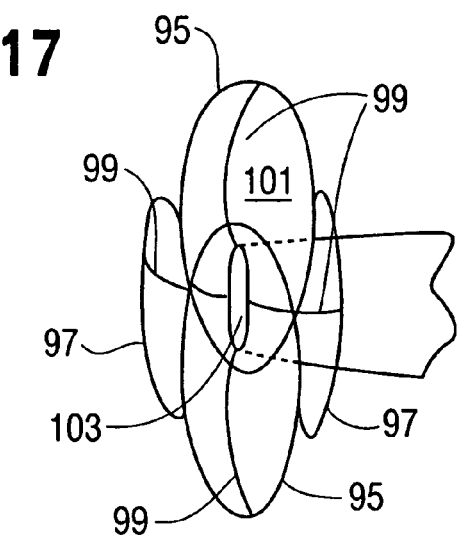
FIG. 17 is a perspective view of a further female condom embodiment in accordance with the present invention, including overlapping circular rings serving as shield-forming external biasing members (plurality of tension vectors also illustrated).

As shown in FIGS. 15–17, multiple outer rings, hoops or other biasing members may be used in non-concentric or overlapping patterns in place of a single outer ring. The biasing members may be contoured or irregular in outline. Any shape that will create a balanced, stable pull on the pouch material and against its "partner" (internal) ring, and be soft and flexible against the skin, may be used.

With reference to FIG. 15, a modified female condom 81 has a plurality of outer biasing members 83 (four shown) formed as multiple soft hoops arranged about central condom opening 85, and serving to resiliently expand opening 85 to an open position. Each hoop 83 has a rounded generally trapezoidal shape such that an inner bottom edge of each hoop lies adjacent condom opening 85. As in the first embodiment, each hoop 83 may be molded integral with the pouch material, or formed separately and joined to the pouch material. Similar to the FIG. 11 embodiment, the multiple hoops and pouch material extending thereacross form a shield-like structure providing greater coverage and protection of the genitals during intercourse. Additionally, with a multiple hoop embodiment, it may be possible to create an outer structure which is softer and more compliant against the skin while exerting a balanced tension force on the pouch membrane.

With reference to FIG. 16, a modified female condom 87 has a plurality of biasing members formed as symmetrically arranged finger-like elements 89, 91 serving as micro-spring hoops. Finger-like elements 89, 91 may be formed integral with or sandwiched within the membranous pouch material 93. A thin web of the membranous pouch material 93 extends within and between the finger-like elements 89, 91 to form a shield-like assembly in generally the same manner as the FIG. 15 embodiment, but with more selective coverage of genital regions. A shape as illustrated may be used to avoid contact with, and pressure on, the clitoris and anus.

FIG. 17 shows yet another overlapping hoop configuration comprising bilaterally symmetrical overlapping circular hoops 95, and arcuate stays 97 joining together lateral sides of hoops 95. Tension vectors 99 extending outwardly from central opening 103 show tension forces imparted to the shield-forming thin membranous pouch material 101.

Figure 18:
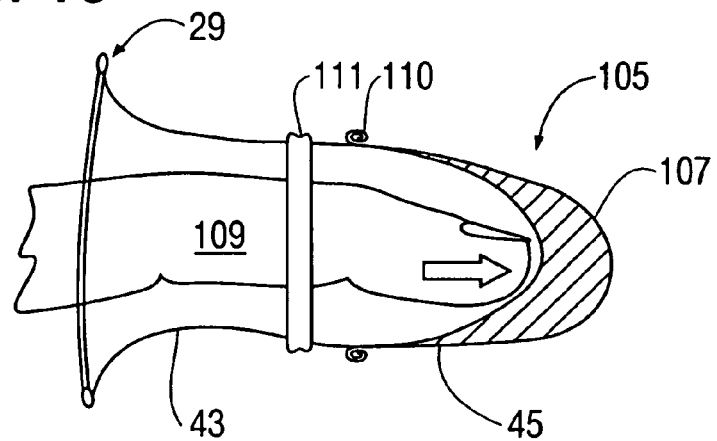
FIG. 18 is a side elevational view (in partial section) of a female condom in accordance with the invention (shown as transparent for clarity), having an insertion/anchoring aid at its closed distal end, and illustrating manual deployment of a pouch of the condom from a roll formed adjacent an inner ring of the condom.

Female condoms in accordance with the present invention may further employ distal end deployment/retaining aids. Referring to FIG. 18, a modified female condom 105 has, as one example, a fluid or gel-filled bag 107 at its closed end, that may serve as one or both of an insertion aid and a distal end anchoring device. Bag 107 is constructed as a double wall structure and may contain air, a lubricant, or a spermicidal fluid. Its outer surface may be coated with a mucosal adhesive to assist with distal end retention on or adjacent the cervix. As shown, a finger 109, or alternatively the partner's penis, may be used to deploy end bag 107 to the cervical region. All or a portion of distal pouch section 45 of female condom 105 may be rolled inwardly upon itself thereby forming a roll 110 of the pouch material adjacent inner ring 111; unrolling deployment of distal pouch section 45 may be effected by insertion of a finger or penis.

Figure 19:
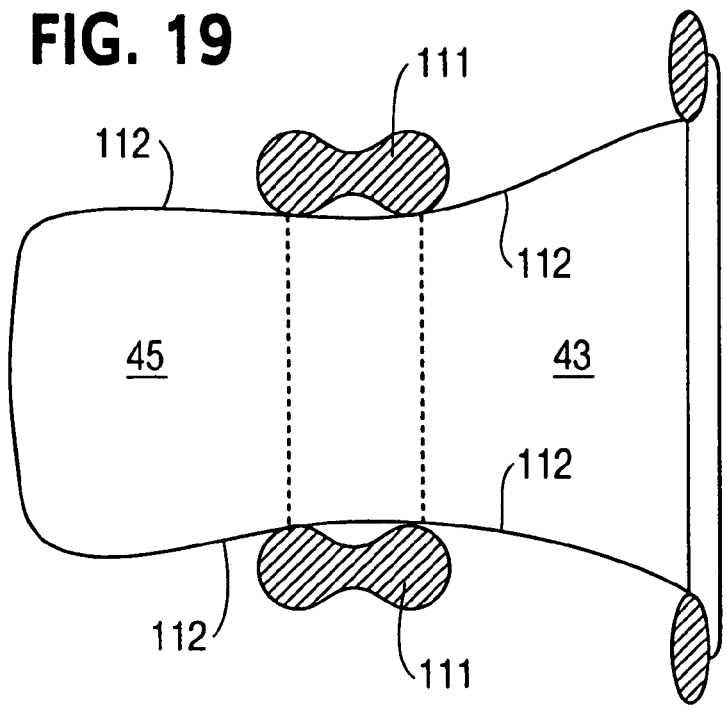
FIGS. 19 and 20 are cross-sectional views of a female condom in accordance with the present invention, illustrating, sequentially, a rolling of membranous pouch material about an inner ring of the condom to achieve an adjustment of inter-ring spacing.
Figure 20:
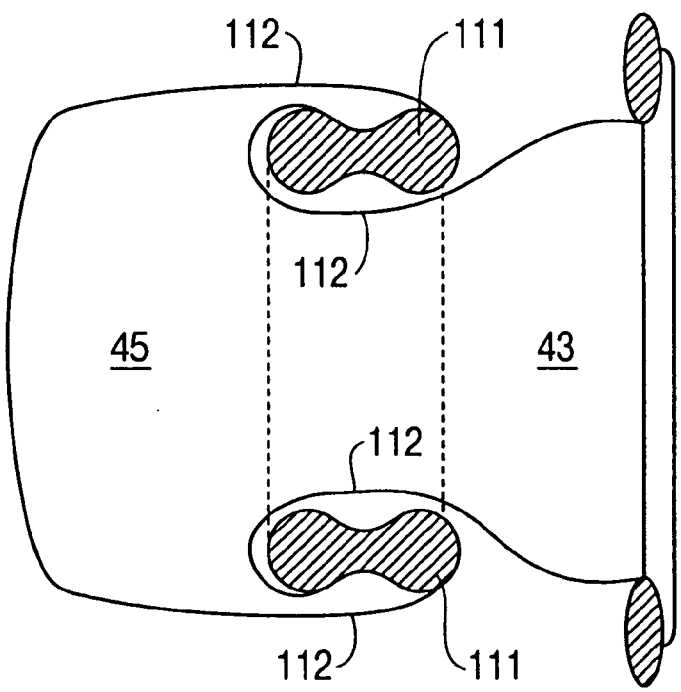

The pouch material may also be selectively rolled onto inner ring 111 to thus enable adjustment of spacing (a) (see FIG. 4) between the inner ring 111 and outer ring 29. As sequentially shown in FIG. 19 and 20, this is accomplished by the user rolling ring 111 and pouch material 112, turning inner ring 111 inside out (180°) at least once. Each time the inner ring turns inside out (180°), it reaches a stable shape/position, with a progressively greater or lesser amount of proximal pouch portion 43 and distal pouch section 45 rolled onto the ring. The adjustment of proximal pouch section 43 permits the condom to be sized to achieve an optimal tensegrity effect taking into account anatomical variation between users. By varying the size and shape of the ring cross-section, the incremental adjustment (per turn) of the inter-ring spacing can be varied.

Figure 21A:
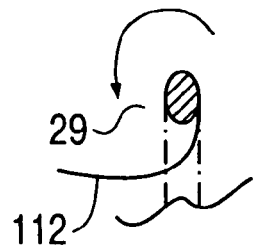
FIGS. 21a–c are partial cross-sectional views of an outer ring of the female condom shown in FIGS. 19 and 20, illustrating, sequentially, a rolling of membranous pouch material about the outer ring to achieve an adjustment of inter-ring spacing.
Figure 21B:
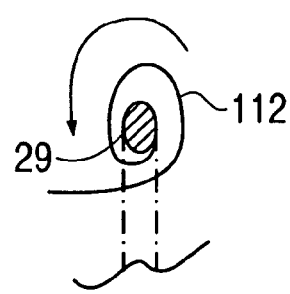
Figure 21C:
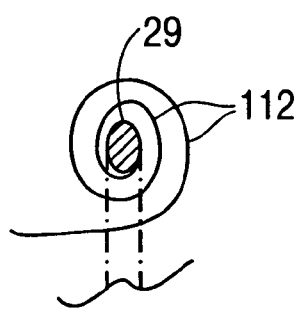

In a similar manner, and as sequentially shown in FIGS. 21a–c, spacing (a) (see FIG. 4) between inner ring 111 and outer ring 29 may be adjusted by selectively rolling pouch material 112 onto outer ring 29, in order to achieve an optimal tensegrity effect. In this case, the incremental adjustment (per turn) of the inter-ring spacing can be varied by varying the size and shape of the cross-section of outer ring 29.

Additional embodiments of the invention are now described with reference to FIGS. 22–27.

Figure 22:
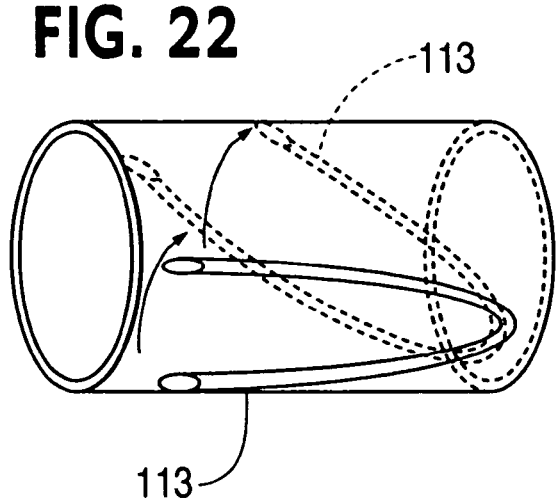
FIG. 22 is a side elevational view of an alternative internal biasing member of the invention, in the form of a tilting elastic stay.

A variation on the elastic stay embodiment of FIG. 14 is a generally U- or V-shaped elastic stay 113 as shown in FIG. 22, mounted (e.g., within a pocket or sleeve formed in or attached to the pouch wall material) so as to permit the stay to be inserted with the arms of the stay extending along opposite sides of the vaginal canal, and then tilted upwardly generally from 30°60° into a position wherein proximal ends of the stay arms (which are preferably enlarged and rounded) may lodge behind the pubic bone of the wearer. In such an embodiment, a manual tilting-up and anchoring of stay 113 reduces reliance on the resilient spring action of stay 113 to assure a proper expansion of the intermediate section of the pouch against a distal portion of the introitus.

It will be appreciated that the internal biasing members of the invention are not limited to the foregoing ring and stay structures, but rather include various other structures providing a resilient bias serving, in use, to expand an intermediate section of the pouch outwardly against a distal portion of the wearer's introitus. Such structures may include asymmetrical elements or elements exhibiting unilateral, bilateral and/or radial symmetry, and which provide correspondingly oriented biasing forces.

As some further examples, the internal biasing member may be a partial or segmented ring structure extending about less than the entire circumference of the pouch. Instead of a relatively narrow ring, partial ring or stay, an internal biasing member may be provided in the form of a pad or pads of resilient material, e.g., foam or sponge-like material, which extends all the way or part-way around the circumference of an intermediate portion of the pouch. Such pad or pads may be formed, e.g., of medical grade foamed polyurethane, and adhered to or integrally formed with the pouch material. It may be desirable to place the pad or pads on an outside of the pouch material, in order to utilize an adherence of the material to the vaginal wall lining, for increasing internal stability of the female condom, and/or reducing reliance on the spring action of the pad material to maintain the intermediate section of the pouch expanded against a distal portion of the introitus. Although non-hydrophilic polyurethane may be used, hydrophilic polyurethane is presently preferred for increasing mucosal cling to the vaginal walls. For the same reason, it may be desirable to use an open cell foam material, which will permit greater moisture absorption as compared to closed cell foam materials.

Figure 23:
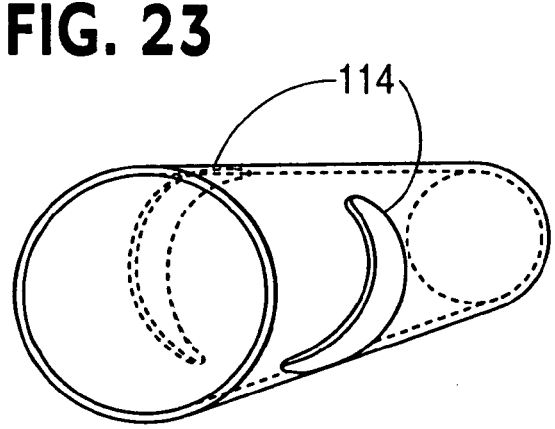
FIG. 23 is a schematic perspective view of an alternative internal biasing member of the invention, in the form of a pair of pads attached to the membranous pouch material.
Figure 24:
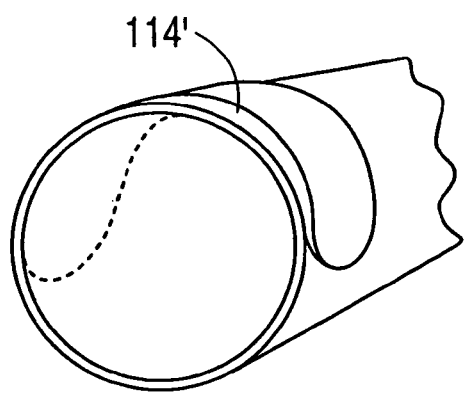
FIG. 24 is a schematic perspective view of an alternative internal biasing member of the invention, in the form of a single pad of material attached to the membranous pouch material.

As shown in FIG. 23, a pair of pads 114, each having a generally crescent-like shape, may be placed in opposition to each other on opposite sides of an intermediate section of the pouch. Alternatively, a single pad 114 could extend around a lower or upper ½–⅔ of the circumference of the pouch, as shown in FIG. 24. The pads 114, 114 may be provided with tapered edges to avoid discomfort and interference due to penile contact during intercourse.

Figure 25:
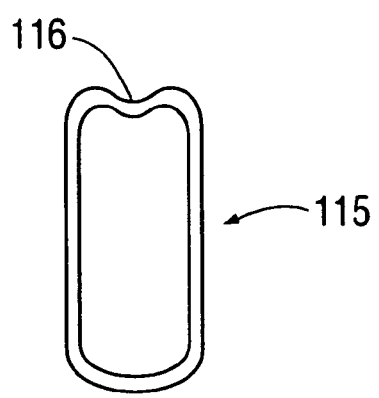
FIG. 25 is a side elevational view of an alternative internal biasing member of the invention, in the form of a ring having a generally oval shape.

Instead of an internal biasing member in the form of a circular ring, other ring shapes may be used, e.g., a generally oval shape ring 115, as shown in FIG. 25, with an aspect ratio of approximately 3:1. In such an embodiment, one end (the upper end in use) of the oval shape may be provided with a notch or indentation 116 serving to avoid contact with, and pressure on, the wearer's urethral opening.

Figure 26:
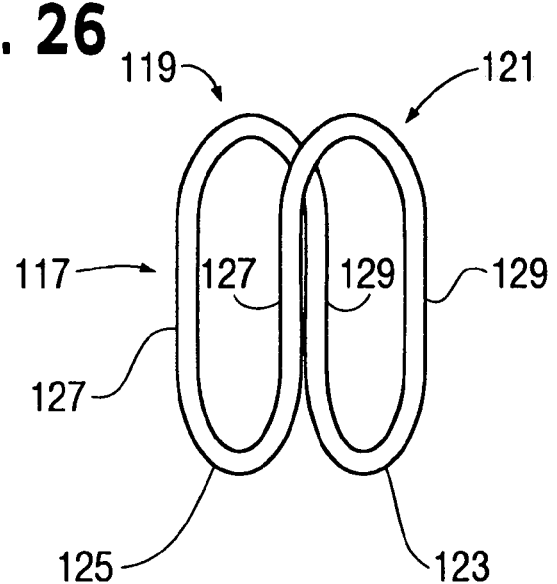
FIG. 26 is a perspective view of an alternative internal biasing member of the invention, in the form of a framework comprising a ring bent over to form a pair of interconnected U-shapes.

Yet another embodiment of the invention comprises an internal biasing member in the form of a ring which is bent over upon itself so that halves thereof form a resilient frame work 117 comprising a pair of U-shapes 119, 121, as shown in FIG. 26. The pair of U-shapes 119, 121 are adjoined by connecting bends 123, 125 at one end, and are spaced from each other at the opposite end. Conversely, the arms 127, 129 within each U-shape 119, 121 are adjoined (in planes orthogonal to connecting bends 123, 125) at the opposite end, and are spaced from each other at the one end. In use, such an internal biasing member is arranged such that the opposite (open) end corresponds to the vaginal floor, with the arms of the U-shapes 119, 121 extending upwardly therefrom, tapering inwardly along the arcuate contour of the expanded pouch material. By providing an open area in the region of the vaginal floor, potentially uncomfortable pressure on the vaginal floor, and the adjacent bowels, can be avoided.

Figure 27:
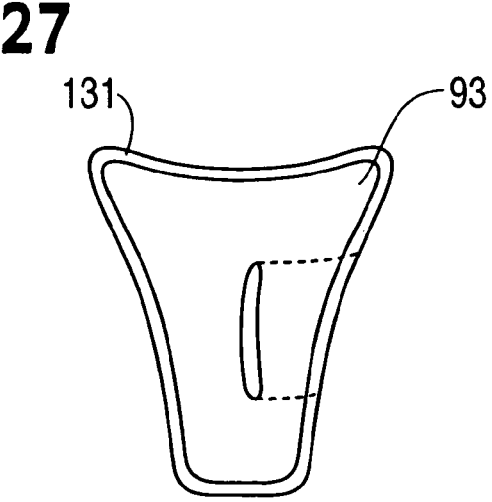
FIG. 27 is a partial perspective view of a further female condom embodiment in accordance with the invention, including an external biasing member in the form of a contoured shield-forming ring.

FIG. 27 shows a variation on the FIG. 16 embodiment, wherein a thin web of membranous material 93 is supported by an external biasing member in the form of a single framing ring 131 following the contoured outer perimeter of material 94, instead of plural finger-like elements 89, 91 which extend inwardly from the outer perimeter and about the central opening of the condom.

The present invention has been described in terms of preferred and exemplary embodiments thereof. Numerous other embodiments, modifications and variations within the scope and spirit of the appended claims will occur to persons of ordinary skill in the art from a review of this disclosure.

The invention claimed is:

1. A female condom, comprising:
   a tubular pouch of resilient membranous material having an open end and a closed end;
   an external biasing member connected to said pouch and providing a resilient bias to expand said open end for retaining, in use, said open end external of a vaginal canal; and
   an internal biasing member connected to said tubular pouch and providing a resilient bias serving, in use, to expand an intermediate section of said pouch outwardly against a distal portion of a woman's introitus;
   said tubular pouch including a distal portion extending between the intermediate section and the closed end, and a proximal portion extending between the open end and the internal biasing member, said internal biasing member being configured and positioned relative to said outer biasing member such that the inner biasing member is, when the condom is installed within a woman's vagina, pushed distally by the introitus to create a force pulling against the outer biasing member, to thereby tent the proximal pouch portion against the introitus in the general shape of an hour-glass;

wherein the internal biasing member forms an outwardly facing recess extending circumferentially at least partially around said intermediate section of said pouch, the internal biasing member comprises a ring, said recess being formed in said ring.

2. The female condom of claim 1, wherein an untensioned spacing between the internal and external biasing members is in the range of 3.75–5.0.

3. The female condom of claim 2, wherein said untensioned spacing is approximately 4.25.

4. The female condom of claim 1, wherein the internal biasing member ring extends circumferentially about said intermediate section of said pouch.

5. The female condom of claim 4, wherein the ring is a circular ring.

6. The female condom of claim 5, wherein an untensioned spacing between the internal and external biasing members is in the range of 3.75–5.0.

7. The female condom of claim 6, wherein said untensioned spacing is approximately 4.25.

8. The female condom of claim 5, wherein the ring has an inner diameter in the range of 1.5"–3.

9. The female condom of claim 4, wherein the ring is a first ring, the external biasing member comprises a second ring, and said first ring is generally concentric with said second ring with respect to a longitudinal axis of the condom.

10. The female condom of claim 9, wherein an untensioned spacing between the first and second rings is in the range of 3.75–5.0.

11. The female condom of claim 10, wherein said untensioned spacing is approximately 4.25.

12. The female condom of claim 4, wherein said first ring has a generally oval shape.

13. The female condom of claim 12, wherein an aspect ratio of said generally oval shape is approximately 3:1.

14. The female condom of claim 12, wherein said generally oval shape has an indentation at one end thereof, for avoiding contact with a urethral opening of a wearer.

15. The female condom of claim 1, wherein the proximal portion of the tubular pouch is pre-formed in the general shape of an hour-glass.

16. The female condom of claim 1, wherein the internal biasing member further comprises a plurality of stay members extending longitudinally along said distal pouch portion and having ends positioned adjacent said intermediate section.

17. The female condom of claim 1, wherein the proximal pouch portion includes a resilient framework extending along said proximal pouch portion between said external and internal biasing members.

18. The female condom of claim 17, wherein the framework includes a plurality of elements extending longitudinally along the proximal pouch portion.

19. The female condom of claim 17, wherein the framework includes an element extending helically along the proximal pouch portion.

20. The female condom of claim 1, wherein said recess is formed as an outwardly facing concave surface of said ring.

21. The female condom of claim 1, wherein said external biasing member comprises a second ring which forms a contoured outer perimeter of a shield-forming portion of said female condom.

22. A female condom, comprising:

a tubular pouch of resilient membranous material having an open end and a closed end;

an external biasing member connected to said pouch and providing a resilient bias to expand said open end for retaining, in use, said open end external of a vaginal canal; and an internal biasing member connected to said tubular pouch and providing a resilient bias serving, in use, to expand an intermediate section of said pouch outwardly against a distal portion of a woman's introitus;

said tubular pouch including a distal portion extending between the intermediate section and the closed end, and a proximal portion extending between the open end and the internal biasing member, said internal biasing member being configured and positioned relative to said outer biasing member such that the inner biasing member is, when the condom is installed within a woman's vagina, rushed distally by the introitus to create a force pulling against the outer biasing member, to thereby tent the proximal touch portion against the introitus in the general shape of an hour-glass;

wherein the internal biasing member forms an outwardly facing recess extending circumferentially at least partially around said intermediate section of said pouch, said internal biasing member comprises a pair of rings connected to each other, said recess being formed between said rings.

23. A female condom, comprising:

a tubular pouch of resilient membranous material having an open end and a closed end;

an external biasing member connected to said pouch and providing a resilient bias to expand said open end for retaining, in use, said open end external of a vaginal canal; and an internal biasing member connected to said tubular pouch and providing a resilient bias serving, in use, to expand an intermediate section of said pouch outwardly against a distal portion of a woman's introitus;

said tubular pouch including a distal portion extending between the intermediate section and the closed end, and a proximal portion extending between the open end and the internal biasing member, said internal biasing member being configured and positioned relative to said outer biasing member such that the inner biasing member is, when the condom is installed within a woman's vagina, pushed distally by the introitus to create a force pulling against the outer biasing member, to thereby tent the proximal pouch portion against the introitus in the general shape of an hour-glass;

wherein the internal biasing member comprises a generally U- or V-shaped elastic stay that can be tilted upwardly, following insertion into said vaginal canal, to lodge behind the wearer's pubic bone.

24. The female condom of claim 23, wherein the internal biasing member further comprises at least one pad of resilient material extending circumferentially at least partially around said intermediate section of said pouch.

25. The female condom of claim 24, wherein said resilient material comprises a foamed material.

26. The female condom of claim 25, wherein said foamed material is a hydrophilic foamed material.

27. The female condom of claim 25, wherein said foamed material comprises foamed polyurethane.

28. A female condom, comprising:

a tubular pouch of resilient membranous material having an open end and a closed end;

an external biasing member connected to said pouch and providing a resilient bias to expand said open end for retaining, in use, said open end external of a vaginal canal; and an internal biasing member connected to said tubular pouch and providing a resilient bias serving, in use, to expand an intermediate section of said pouch outwardly against a distal portion of a woman's introitus;

said tubular pouch including a distal portion extending between the intermediate section and the closed end, and a proximal portion extending between the open end and the internal biasing member, said internal biasing member being configured and positioned relative to said outer biasing member such that the inner biasing member is, when the condom is installed within a woman's vagina, pushed distally by the introitus to create a force pulling against the outer biasing member, to thereby tent the proximal pouch portion against the introitus in the general shape of an hour-glass;

wherein the internal biasing member comprises a ring which is bent over upon itself to form a resilient framework comprising a pair of generally U-shaped members.

29. A method of maintaining a female condom within a vaginal canal of a woman, the female condom including a tubular pouch of resilient membranous material having an open end and a closed end, an external biasing member, and an internal biasing member, said method comprising the steps of:

inserting a portion of the female condom, including the internal biasing member, into the vaginal canal; and permitting the internal biasing member to expand an intermediate section of the condom positioned within the vaginal canal at a distal portion of the woman's introitus, and the woman's introitus to exert inward compressive forces on a proximal portion of the tubular pouch extending between the open end and the intermediate section, such that said proximal portion pulls proximally on the internal biasing member while the introitus presses distally against the internal biasing member, whereby the proximal portion is tented against the introitus.

30. A method according to claim 29, wherein said inserting is carried out by inserting a tubular inserter device into the vaginal canal to place a distal end of the device proximal the distal portion of the introitus, advancing a plunger of the device within an outer housing of the device to cause the internal biasing member to exit the device from said distal end, and withdrawing the device away from the vaginal opening with said internal biasing member retained by the introitus.

31. The method of claim 29, further comprising adjusting the size of the female condom, said adjusting comprising adjusting a spacing between said external biasing member and said internal biasing member by rolling said resilient membranous material upon one of said external biasing member and said internal biasing member.

32. A method according to claim 31, wherein said one of said external biasing member and said internal biasing member comprises a ring, and said rolling is carried out by turning said ring inside out (180°) at least once.

33. An assembly for preplacing a female condom within a vaginal canal of a woman, said assembly comprising:

an inserter device including a tubular housing and a plunger member advanceable within said housing; and a female condom enclosed within said inserter device in a collapsed condition such that upon advancement of said plunger member at least a portion of said female condom is pushed out of said tubular housing by said plunger member and permitted to expand from said collapsed condition;

wherein a proximal end of said female condom extends within said plunger member;

wherein said plunger member comprises a ledge serving to push a distal end of said female condom disposed generally opposite said proximal end out of said tubular housing as said plunger member is advanced within said tubular housing, said ledge permitting said proximal end of said tubular pouch to pass thereby and out of said tubular housing after said distal end has been pushed out of said tubular housing.

34. The assembly of claim 33, wherein said female condom comprises a tubular pouch and a first pouch biasing member, and said advancement of the plunger member pushes a distal portion of said tubular pouch, and said first pouch biasing member, out of a distal end of said tubular housing.

35. The assembly of claim 34, wherein a proximal portion of said tubular pouch extends within said plunger member.

36. The assembly of claim 35, wherein said plunger member comprises a ledge serving to push said first pouch biasing member out of said tubular housing as said plunger member is advanced within said tubular housing, said ledge permitting said proximal portion of said tubular pouch to pass thereby and out of said tubular housing after said first pouch biasing member has been pushed out of said tubular housing.

37. The assembly of claim 36, wherein said female condom further comprises a second pouch biasing member connected to said proximal portion.

* * * * *

UNITED STATES PATENT AND TRADEMARK OFFICE
CERTIFICATE OF CORRECTION

PATENT NO. : 7,047,975 B2  Page 1 of 1
APPLICATION NO. : 09/921016
DATED : May 23, 2006
INVENTOR(S) : Glenn D. Austin et al.

It is certified that error appears in the above-identified patent and that said Letters Patent is hereby corrected as shown below:

On the cover page, Assignee section (73):
　　　Please replace "Path" with --PATH--

In Column 15, Claim 12, Line 37:
　　　Please replace "first ring" with --ring--

In Column 16, Claim 22, Line 19:
　　　Please replace "rushed" with --pushed--

In Column 16, Claim 22, Line 21:
　　　Please replace "touch" with --pouch--

Signed and Sealed this

First Day of July, 2008

JON W. DUDAS
*Director of the United States Patent and Trademark Office*